(12) United States Patent
Tam (10) Patent No.: US 7,972,494 B2
(45) Date of Patent: Jul. 5, 2011

(54) APPLICATION OF BIOSENSOR CHIPS

(75) Inventor: Simon Tam, Cambridgeshire (GB)

(73) Assignee: Seiko Epson Corporation, Tokyo (JP)

( * ) Notice: Subject to any disclaimer, the term of this patent is extended or adjusted under 35 U.S.C. 154(b) by 1283 days.

(21) Appl. No.: 11/589,137

(22) Filed: Oct. 30, 2006

(65) Prior Publication Data
US 2007/0102304 A1    May 10, 2007

(30) Foreign Application Priority Data
Nov. 9, 2005  (GB) .................................. 0522894.5

(51) Int. Cl.
*G01N 27/327*  (2006.01)
*C12Q 1/68*  (2006.01)

(52) U.S. Cl. ...................... 205/777.5; 205/792; 422/50

(58) Field of Classification Search .............. 204/403.01–403.15; 205/777.5, 205/778, 792; 422/55–58
See application file for complete search history.

(56) References Cited

U.S. PATENT DOCUMENTS

| | | | |
|---|---|---|---|
| 4,244,458 A * | 1/1981 | Kampf | 198/346.2 |
| 5,545,531 A | 8/1996 | Rava et al. | |
| 5,711,862 A * | 1/1998 | Sakoda et al. | 204/403.05 |
| 5,981,166 A * | 11/1999 | Mandecki | 435/4 |
| 6,280,587 B1 * | 8/2001 | Matsumoto | 204/403.01 |
| 6,331,441 B1 | 12/2001 | Balch et al. | |
| 6,617,963 B1 | 9/2003 | Watters et al. | |
| 6,806,808 B1 | 10/2004 | Watters et al. | |
| 7,034,660 B2 | 4/2006 | Watters et al. | |
| 7,157,050 B2 * | 1/2007 | Yazawa et al. | 422/68.1 |
| 7,341,834 B2 | 3/2008 | Yang | |
| 7,659,983 B2 * | 2/2010 | Moon et al. | 356/417 |
| 2001/0049147 A1 | 12/2001 | Bierre et al. | |
| 2002/0057097 A1 | 5/2002 | Kelly et al. | |
| 2002/0065576 A1 | 5/2002 | Beaucour | |
| 2003/0033032 A1 | 2/2003 | Lind et al. | |
| 2004/0120861 A1 | 6/2004 | Petroff | |
| 2004/0121354 A1 | 6/2004 | Yazawa et al. | |
| 2004/0173456 A1 * | 9/2004 | Boos et al. | 204/403.02 |
| 2004/0230488 A1 | 11/2004 | Beenau et al. | |
| 2004/0233039 A1 | 11/2004 | Beenau et al. | |
| 2004/0233043 A1 | 11/2004 | Yazawa et al. | |
| 2004/0233054 A1 | 11/2004 | Neff et al. | |
| 2004/0238623 A1 | 12/2004 | Asp | |

(Continued)

FOREIGN PATENT DOCUMENTS

DE    103 51 412 B3    1/2005

(Continued)

OTHER PUBLICATIONS

Hashimoto et al. "Sequence-specific gene Detection with a Gold Electrode Modified with DNA Probes and an Electrochemically Active Dye," Anal. Chem. 1994, 66, 3830-3833.*

(Continued)

*Primary Examiner* — Alex Noguerola
(74) *Attorney, Agent, or Firm* — Oliff & Berridge, PLC (57) ABSTRACT

A method of sensing a property of each of a plurality of samples is disclosed. The method includes disposing a sensor chip in each sample, the sensor chip being adapted to sense the property of a respective sample and comprising sensing electronics, a wireless communication device and an identifier. Each sensor chip is then registered and sensed data is received from each of the registered sensor chips concurrently via the respective wireless communication device.

10 Claims, 6 Drawing Sheets

U.S. PATENT DOCUMENTS

| | | |
|---|---|---|
| 2004/0239480 A1 | 12/2004 | Beenau et al. |
| 2004/0249499 A1 | 12/2004 | Green |
| 2006/0141474 A1 | 6/2006 | Miyahara et al. |
| 2006/0170535 A1 | 8/2006 | Watters et al. |
| 2008/0210573 A1 | 9/2008 | Yang |

FOREIGN PATENT DOCUMENTS

| | | |
|---|---|---|
| EP | 1 396 725 A1 | 3/2004 |
| GB | 2 386 949 A | 10/2003 |
| JP | A 2001-147231 | 5/2001 |
| JP | A-2002-538519 | 11/2002 |
| JP | A 2004-139345 | 5/2004 |
| JP | A-2005-077210 | 3/2005 |
| WO | WO 99/28724 | 6/1999 |
| WO | WO 01/94016 A1 | 12/2001 |
| WO | WO 03/083905 A2 | 10/2003 |
| WO | WO 2004/037405 A1 | 5/2004 |
| WO | WO 2004/053491 A1 | 6/2004 |

OTHER PUBLICATIONS

Baard, Mark. "USA: Biosensors to be Used for Homeland Security." *CorpWatch*, Aug. 26, 2003.

Shih, Wim. "Radio-Frequency Identification: Waving in "the Oldest New Technology"." *Pharmaceutical International*, Dec. 13, 2003.

Office Action in U.S. Appl. No. 12/073,875, dated Jul. 1, 2010.

Office Action issued in U.S. Appl. No. 12/073,875 on Nov. 19, 2010.

* cited by examiner

| | | | | |
|---|---|---|---|---|
| <u>V</u> | A | B | C | D | 
| <u>W</u> | F | P | Q | |
| <u>X</u> | A | B | C | D | E |
| <u>Y</u> | G | I | | |
| <u>Z</u> | J | K | L | M | N |

BASE REGISTER

<No. of Samples in Holder>
Sample 1
<Sample Holder Chip ID>
<Date and Time Stamp>
<No. of Sensor Chips>
<Status Flags>
Chip1
<Chip ID>
<Status Flags>
<No. of Data Sets>
<Data Set 1>
<Data Set 2>
...
<Data Set N>
Chip2
<Chip ID>
<Status Flags>
<No. of Data Sets>
<Data Set 1>
<Data Set 2>
...
<Data Set N>
...
Sample 2
...

CHIP REGISTER

<Chip ID>
<No. of Data Sets to Transmit>
<Status Flags>
<Seed for Random Number>
<Size of Data Sets>

APPLICATION OF BIOSENSOR CHIPS

FIELD OF THE INVENTION

Several aspects of the present invention relates to sensor chips and a method and apparatus for sensing concurrently one or more properties of each of a plurality of samples. Preferably the samples are biological samples and the sensors are biosensors.

BACKGROUND OF THE INVENTION

Figure 1A:
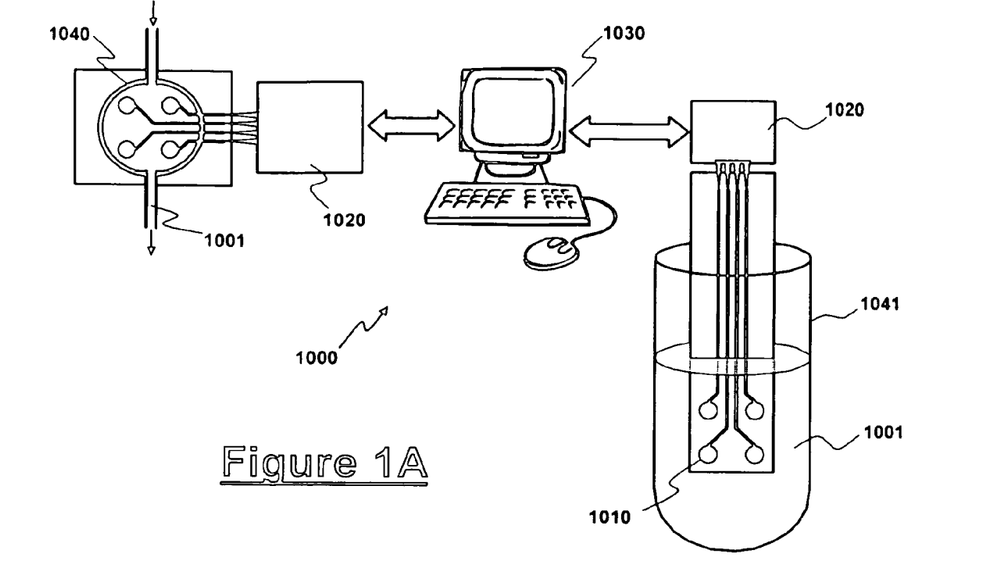
FIGS. 1A-C show a conventional biosensor system.

As shown in FIG. 1A, a conventional biosensor system 1000 typically includes an array of biosensors 1010 for interaction with a buffer solution 1001 that contains the biomaterial under test. The system further includes signal preamplifiers and driving circuits 1020, which are disposed outside the solution 1001 and are connected to the respective biosensors 1010. The signal preamplifiers and driving circuits 1020 are connected to a data analysis and storage unit, such as a computer 1030.

Figure 1B:
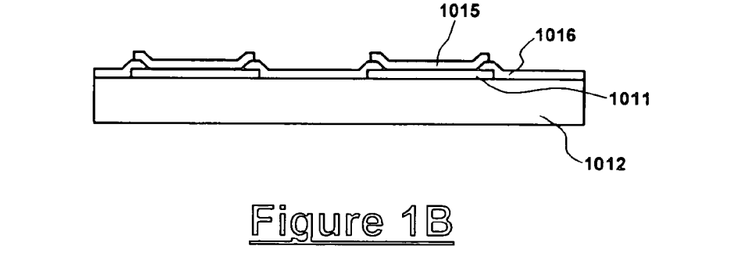

A typical array of biosensors 1010 is shown in cross-section in FIG. 1B, in which a plurality of gold electrodes 1011 are formed on a glass substrate 1012. Typically, these electrodes are connected to the signal preamplifiers and driving circuits 1020 by using suitable connectors or via a set of probing needles. To prevent short circuit, the glass substrate 1012 and gold electrodes 1011 are passivated using a suitable passivation material 1016, with openings over portions of the gold electrodes 1011. Different types of bioreceptive layer 1015 (commonly known as a probe) are formed covering each of the gold electrodes where exposed by the openings 1011 to interact with the biomaterial under test (commonly known as a target). Specifically, the bioreceptive layer may be a phage or enzyme that binds with a predetermined DNA or RNA strand, a peptide or another biological molecule, thereby changing the resistance and/or the capacitance of the circuit in which the electrode is connected. These changes can be detected in turn to establish whether the predetermined biological molecule is present, and even its concentration. The reliability of detection can be enhanced by increasing the number of different bioreceptive layers, which allows cross-referencing and cross-elimination in the data analysis process.

The use of gold for the electrodes 1011 enhances the adhesion of the materials used to form the bioreceptive layer 1015, and the electrodes 1011 are spaced at a sufficient separation to reduce the effects of cross-talk.

On the left side of FIG. 1A, the array of biosensors is disposed in a flow cell 1040, in which the solution or sample 1001 to be analysed is passed over the array, in a direction indicated by the arrow. On the right side of FIG. 1A, the array of biosensors is submerged in a container, such as a test tube 1041, in which the solution or sample 1001 containing biomaterial under test is held.

Although generally found to be effective, there are commonly problems in such arrangements in that the comparatively long signal path due to the wiring between the electrodes and the signal pre-amplification and driving circuits 1020 picks up noise, thereby reducing the signal-to-noise ratio and greatly limiting the system sensitivity.

This problem has been mitigated at least to an extent by integrating the pre-amplification and driving circuitry with the sensors on the chip. A schematic representation of this is shown in cross-section in FIG. 1C. This figure is the same as FIG. 1B in most respects and like reference numerals indicate like parts. However, FIG. 1C further shows a Thin Film Transistor (TFT) chip 1050 provided on the glass substrate 1012, the illustrated TFT comprising a gate 1051, source 1052, drain 1053 and channel 1054. Of course, a plurality of TFTs can be provided on the sensor chip and interconnected to provide the desired pre-amplification and driving operations. In addition, other forms of transistor technology, such as CMOS, are possible.

Figure 1C:
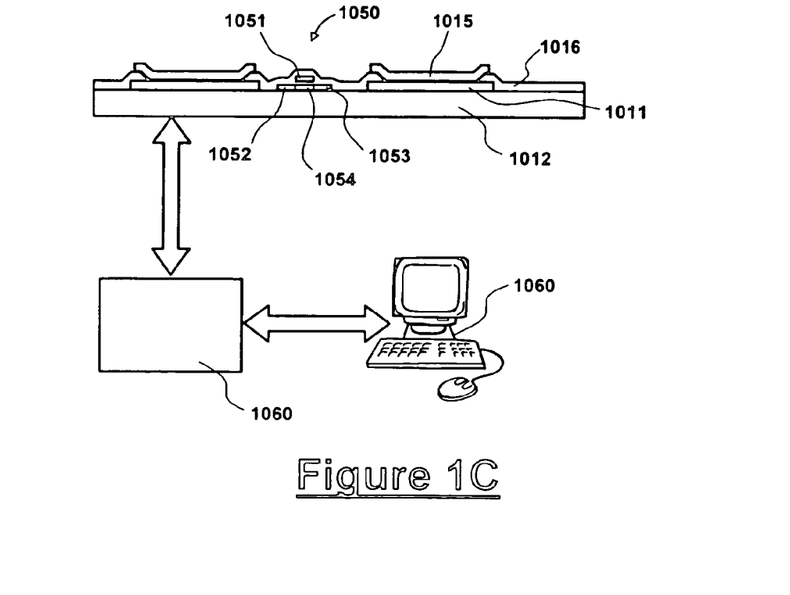

The integration of the pre-amplification and driving circuitry on the chip has the significant advantage of an increase in signal-to-noise ratio. Therefore, for a fixed concentration of sample solution, this integration will require smaller probe areas, which is beneficial in quality control applications. The sensitivity of the probe is also improved, which is beneficial for medical applications when the volume of sample is limited in supply. However, as shown in FIG. 1C, this implementation still requires external electronics 1060 for the detection and relay of signals from the sensor chip to the computer 1030. This is a significant obstacle in terms of size and set up cost.

Figure 2A:
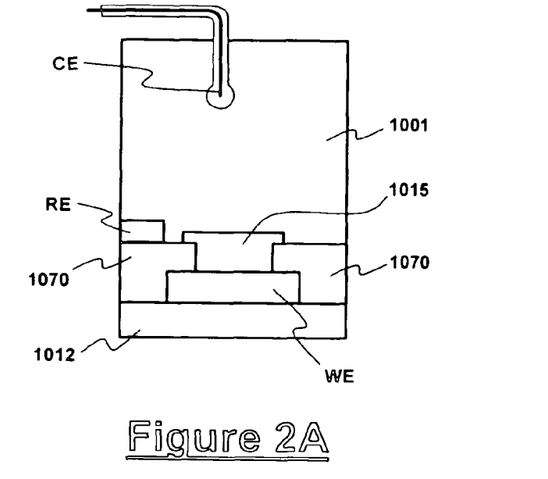
FIG. 2A shows a potentiostat circuit.
Figure 2B:
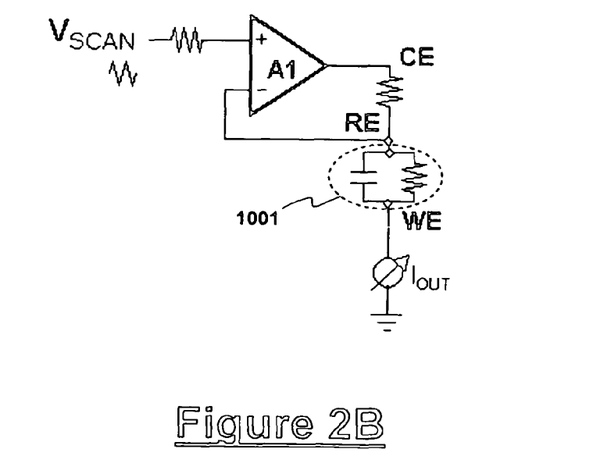
FIG. 2B shows an electrical representation of the potentiostat circuit in FIG. 2A.

In the implementations shown in both FIGS. 1B and 1C, the pre-amplification and driving circuits to which the electrode is connected is typically a potentiostat. A physical representation of a prior art potentiostat circuit is shown in FIG. 2A. and an electrical representation is shown in FIG. 2B. As shown in FIG. 2A, the potentiostat circuit consists of three electrodes: a counter electrode CE, a reference electrode RE and a working electrode WE. The electrodes are connected to an electrochemical cell, which is realised by a buffer solution with the biomaterial 1001 between counter electrode CE and reference electrode RE, and a bioreceptive layer 1015 between reference electrode RE and working electrode WE. An equivalent circuit of the three terminal electrochemical cell is given in FIG. 2B. In essence, the potentiostat circuit measures the current at working electrode WE due to a redox reaction at the bioreceptive layer while RE is kept at a known voltage. Counter electrode CE is provided to supply the necessary current to maintain reference electrode RE at a known voltage. Many versions of potentiostat are known and a multi-channel potentiostat is known for the measurement of a matrix of samples. The applied input voltage changes the redox (reduction-oxidation) reaction at the bioreceptive layer, which in turn changes the effective values of the capacitance and resistance of the equivalent circuit, allowing the detection of the presence of a target biological molecule and its concentration.

Figure 2C:
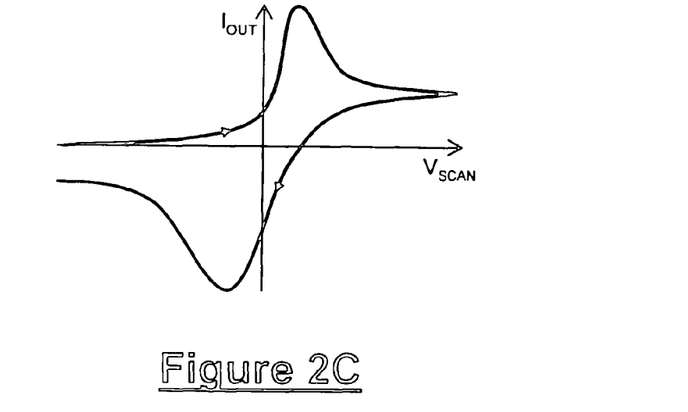
FIG. 2C shows a typical output from the potentiostat circuit in FIG. 2A for a reversible redox reaction.

Cyclic voltammetry is a technique commonly employed in a potentiostatic measurement. Here, the voltage at RE, shown as $V_{SCAN}$ in FIG. 2B, is a triangular wave. During the first half cycle, a reduction (or oxidation) reaction is dominant, diffusion occurs due to different concentration of the reduced and oxidised species, and the net current flow is reflected as a peak at the output. During the second half cycle, if the redox reaction is reversible, an oxidation (or reduction) reaction occurs, and a peak current of the same magnitude but in the opposite direction can be seen at the output. A typical output for a reversible redox reaction is given in FIG. 2C. It is of importance to note the height and locations of any peaks in such an output.

Some redox reactions can be particularly slow and therefore time-consuming to complete a measurement. The measurement of a large number of redox reactions for different target biological molecules under different conditions can therefore be highly problematic.

However, the present invention is not limited to potentiostat circuits. Other means of measuring or sensing properties of a sample can also be used. One such means is a pH sensor, which typically includes an ion-sensitive field effect transistor (ISFET) with an exposed gate in contact with the sample solution, the drain-source current of which is found to be related to the concentration of $H^+$ ions in the solution. Since the concentration of $H^+$ ions is indicative of pH, the pH of the sample solution can be measured.

The use of RFID (radio frequency identification) circuits in biosensor chips is also known. This removes the requirement for a physical interconnection between the sensor chips 1010 and the data analysis and storage computer 1030. However, problems still remain with the speed and throughput with which samples of solutions can be measured, which leads to increased costs and backlogs in hospitals and other laboratories, together with the problems concomitant with such backlogs. This is a particular problem with measurements of redox reactions of bioreagents, which tend to be slow. It is therefore very time-consuming to complete all measurements in an array of electrodes.

RFID devices are either active, wherein the device includes a power supply, or passive, wherein the device extracts power from received radio signals and uses this to power itself.

SUMMARY OF THE INVENTION

Several aspects of the present invention has been made with a view to overcoming the problems inherent in existing devices and especially in the speed and throughput with which samples of solutions can be measured.

According to a first aspect of the present invention, there is provided method of sensing at least one property of each of a plurality of samples, the method comprising:

disposing at least one sensor chip in each sample, said at least one sensor chip being adapted to sense at least one said property of a respective sample and comprising sensing electronics, a wireless communication device and an identifier;

registering each sensor chip; and receiving sensed data from each of the registered sensor chips concurrently via the respective wireless communication device.

Preferably, the method further includes adding a further sample to the plurality of samples by registering each sensor chip in the further sample and receiving sensed data from the sensor chips in the further sample concurrently with the sensed data from the plurality of samples.

Preferably, the method further includes establishing when the sensed data from a sensor chip in a respective sample has been successfully received and the at least one property sensed by this sensor chip has been determined; and when this established for each sensor chip in the respective sample, removing the respective sample from the plurality of samples.

Preferably, each sample is provided with a wireless communication device, an identifier and an indicator and, when it is established for each sensor in a sample that the respective at least one property has been determined, setting the indicator to indicate that sensing for the sample has been finished.

Preferably, the step of registering each sensor in a sample includes disposing the sample in a sensing area.

Preferably, the step of registration includes searching in a sensing area for sensor chips having previously unrecognised identifiers and registering each such sensor chip.

Preferably, the method further includes previously recording the identifier, or a portion of the identifier, of each sensor chip and associating the identifier, or the portion of the identifier, with the at least one property that the sensor chip is adapted to sense, whereby when the sensor chip is registered the at least one property sensed by the sensor chip is known.

Preferably, upon registration each sensor chip transmits via its wireless communication device the at least one property that it is adapted to sense.

Preferably, the step of receiving data from each of the sensor chips in a sample includes polling each registered sensor chip to determine whether it has sensed data ready for transmission.

Preferably, at least one of said sensor chips is a biosensor chip. More preferably, the biosensor chip is adapted to sense for one or more of DNA, RNA, a gene sequence, a peptide and another biological molecule. Still more preferably, the biosensor chip includes one or more potentiostat circuits. Yet more preferably, a counter electrode is provided for each potentiostat circuit in a sample by applying a bias voltage to the sample.

Preferably, the sensor chip is used for sensing one or more said properties of a sample using a redox reaction.

Preferably, the method further includes disposing a respective sample in a sensing area, the sensing area adapted to control one or more predetermined conditions of the sample. More preferably, the sensing area includes at least one of a heater, a cooler, a temperature-controlled fluid bath, an agitator and a means for controlling flow of a fluid to be sampled over the sensor chips.

Preferably, the step of registering is carried out before the step of disposing the sensor chips in a respective sample.

Preferably, the communication device and the identifier of each sensor chip include RFID electronics.

Preferably, the step of registering includes associating each sensor chip with a respective sample.

According to another aspect of the present invention, there is provided an apparatus for sensing at least one property of each of a plurality of samples concurrently, comprising:

a sensing area;

a wireless communication device for wirelessly transmitting signals to and receiving signals from each of a plurality of sensor chips within the sensing region, each sensor chip being disposed in a respective sample, being adapted to sense at least one said property of the respective sample and comprising sensing electronics, a sensor chip wireless communication device and an identifier;

a register for registering the identifier of each sensor chip; and a sensed data processor for receiving and processing sensed data from each of the registered sensor chips concurrently via the sensor chip wireless communication devices.

Preferably, the register is adapted to register associated data of each sensor chip, including at least one of the samples in which the sensor chip is disposed and the at least one property which the sensor chip is adapted to sense.

Preferably, the register and the sensed data processor are adapted to perform operations concurrently.

Preferably, the sensed data processor is adapted to establish when the at least one property of a respective sample sensed by a sensor chip has been determined; and indicate when it is established for each sensor in a sample that the respective at least one property has been determined.

Preferably, the apparatus further includes a loader for loading each sample into the sensing area before registration and for removing each sample from the sensing area after it is established for each sensor chip in that sample that the respective at least one property has been determined. More preferably, the loader is adapted to dispose predetermined sensor chips in each sample before or after loading the sample into the sensing area.

As an alternative, each sample is provided with a wireless communication device, an identifier and an indicator, and the sensed data processor is adapted to establish for all sensor chips in a sample when the respective at least one property has been determined, and to set the indicator to indicate that sensing for the sample has finished.

Preferably, the register has previously recorded in it the identifier, or a portion of the identifier, of each sensor chip and associated with the identifier, or the portion of the identifier, the at least one property that the sensor chip is adapted to sense, whereby when the sensor chip is registered the at least one property sensed by the sensor chip is known.

Preferably, upon registration each sensor chip transmits the at least one property that it is adapted to sense to the antenna via its wireless communications means for registration.

Preferably, the apparatus is arranged to poll each registered sensor chip to determine whether it has sensed data for transmission.

Preferably, at least one of said sensor chips is a biosensor chip. More preferably, the sensed data relates to at least one of DNA, RNA, a gene sequence, a peptide and another biological molecule. Yet more preferably, the biosensor chip includes one or more potentiostat circuits and wherein the apparatus is arranged to apply a bias voltage to a sample in which the biosensor chip is disposed to provide a counter electrode for each potentiostat circuit of the biosensor chip.

Preferably, at least one sensor chip is used for sensing said at least one property of a sample during a redox reaction.

Preferably, the apparatus is adapted to control at least one condition of samples in a sensing area. More preferably, the sensing area includes at least one of a heater, a cooler, a temperature-controlled fluid bath, an agitator and a means for controlling flow of a fluid to be sampled over the sensor chips.

Preferably, the register is adapted to register the sensor chips before they are disposed in a respective sample.

Preferably, the communication device and the identifier of each sensor chip include RFID electronics.

According to a further aspect of the present invention, there is provided a sensor chip having integrated in it sensing electronics, a wireless communication device, an identifier and a memory, wherein the memory is for storing sensed data and the sensor chip is adapted to transmit the identifier and sensed data stored in the memory.

BRIEF DESCRIPTION OF THE DRAWINGS

The present invention will now be described by way of example only with reference to the accompanying drawings, in which.

DETAILED DESCRIPTION

Figure 7A:
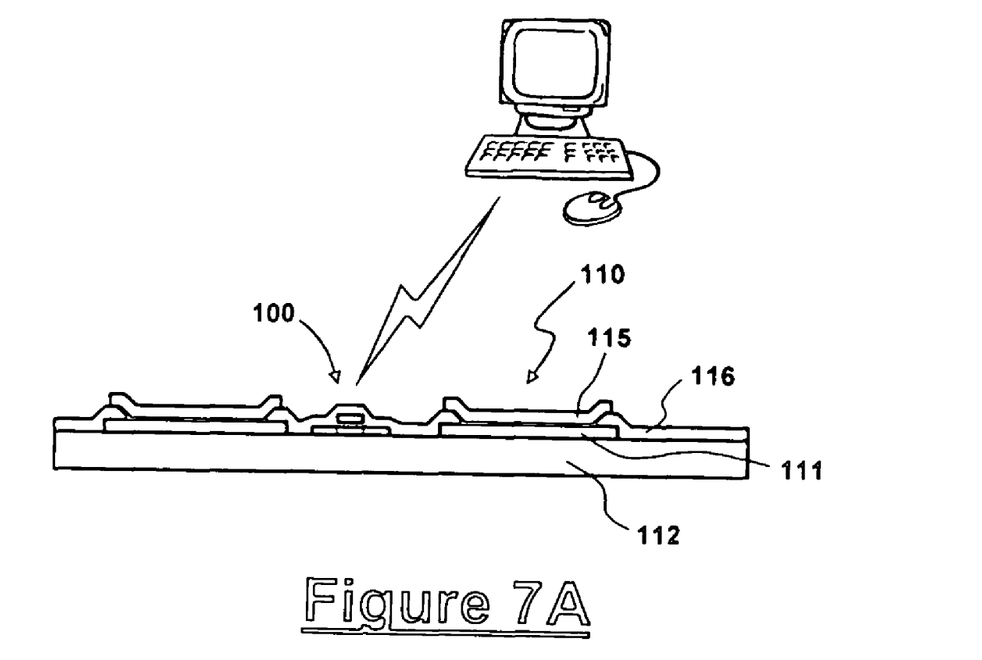
FIGS. 7A & B are a representation of a biosensor system according to an aspect of the present invention.
Figure 7B:
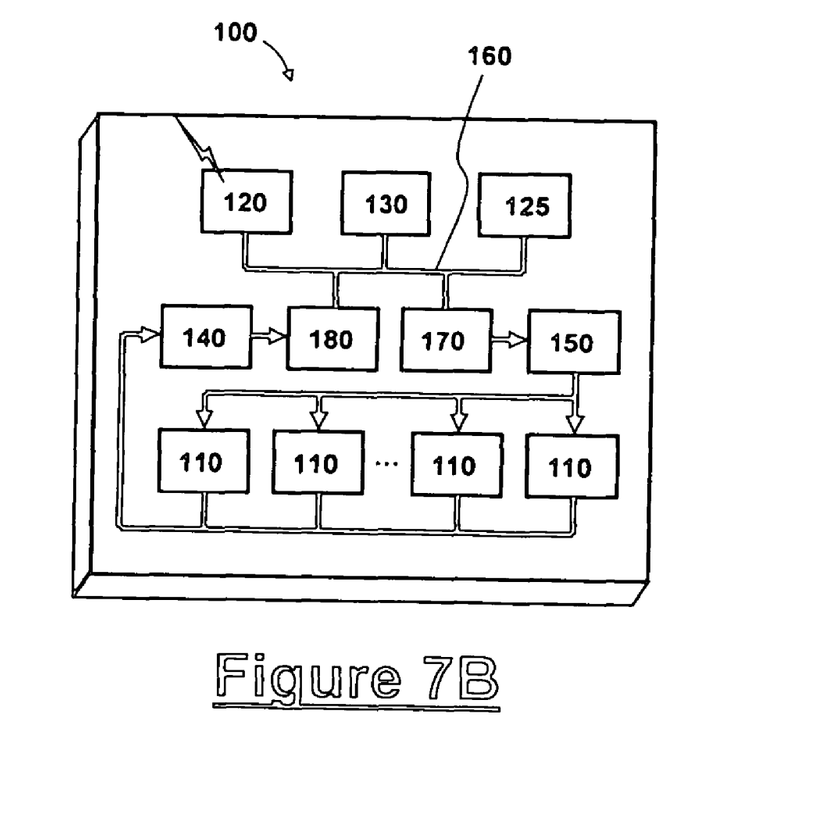

FIG. 7 shows a sensor device in accordance with one aspect of the present invention. Specifically, FIG. 7A shows a biosensor chip comprising a plurality of sensors 110 arrayed on a glass substrate 112. Each sensor consists of a region of bioreceptive layer 115 covering a via hole above a gold electrode 111 in a continuous layer of a suitable passivation material 116 over the entire chip. Each bioreceptive layer 115 will interact differently with the biomaterial in the solution under test, and redox reactions will take place when voltages are applied during the measurements. In addition, the sensor chip includes circuitry 100 represented by a TFT integrated in the chip. As shown in FIG. 7B, the circuitry 100 includes a microcontroller or processor 125, RFID electronics 120, pre-amplification circuitry 140, driving circuitry 150, a memory 130, digital-to-analogue converters 170 and analogue-to-digital converters 180. These components are connected by means of a bus 160 under control of the microcontroller or processor 125. Signals from each of the sensors 110 are fed to the pre-amplification circuitry 140 under control of the driving circuitry 150. The signals from the respective biosensors, which represent sensed data, are stored under control of the processor 125 in the memory 130 for subsequent transmission to a base station using the RFID circuitry 120. Specifically, the base station will poll each sensor chip to request for sensed data. If the sensed data is ready, the base station instructs the processor 125 to transmit the sensed data for each of the sensors 110, or at least those sensors for which data is stored, to the base station for subsequent analysis.

Figure 3:
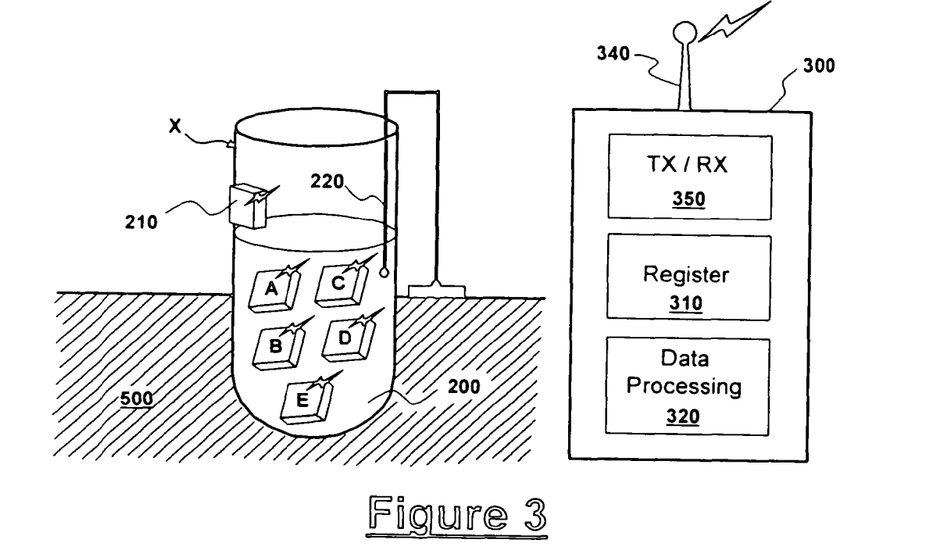
FIG. 3 shows biosensor system according to one aspect of the present invention.

In the present invention, a plurality of such sensor chips may be disposed in a solution or sample for analysis. Each of the sensor chips may be for sensing one or more different properties of the sample solution. Thus, FIG. 3 shows a sample X, for example of urine, which will have in it a number of different biological molecules. Sensor chips A-E are disposed in the urine sample for detecting respective properties of it. For example, sensor chip A may be for detecting glucose concentration; sensor chips B and C for detecting first and second sets of gene sequences; sensor chip D for detecting a particular peptide; and sensor chip E for detecting a particular virus. Each sensor chip A-E has the circuitry 100 shown in FIG. 7B.

The sample X is disposed in a holder 500 of a sensing system of the present invention in relation to a base station 300. The base station includes a register or memory 310 and a data processing section 320, as well as transmitter/receiver (transceiver) circuits 350 and an antenna 340. By means of the antenna 340 and transceiver circuits 350, the base station 300 is able to communicate with each of the sensor chips A-E in sample X. In addition, the RFID circuitry 120 on each of the sensor chips is able to extract power from the radio frequency signals emitted by the antenna and hence to power not only the sensing, pre-amplification and driving circuitry but also the transmission of signals to the antenna 340 of the base station 300.

In a preferred embodiment, sample X is also provided with a passive RFID tag 210, by which the sample can be identified as distinct from the sensor chips in the sample.

In the event that one or more of the sensor chips A-E in sample X includes a potentiostat circuit, an electrode 220 is disposed in the sample to apply a bias voltage to it. Accordingly, the electrode 220 acts as the common counter electrode CE for all potentiostat circuits on the chips included in sample X.

Figure 4A:
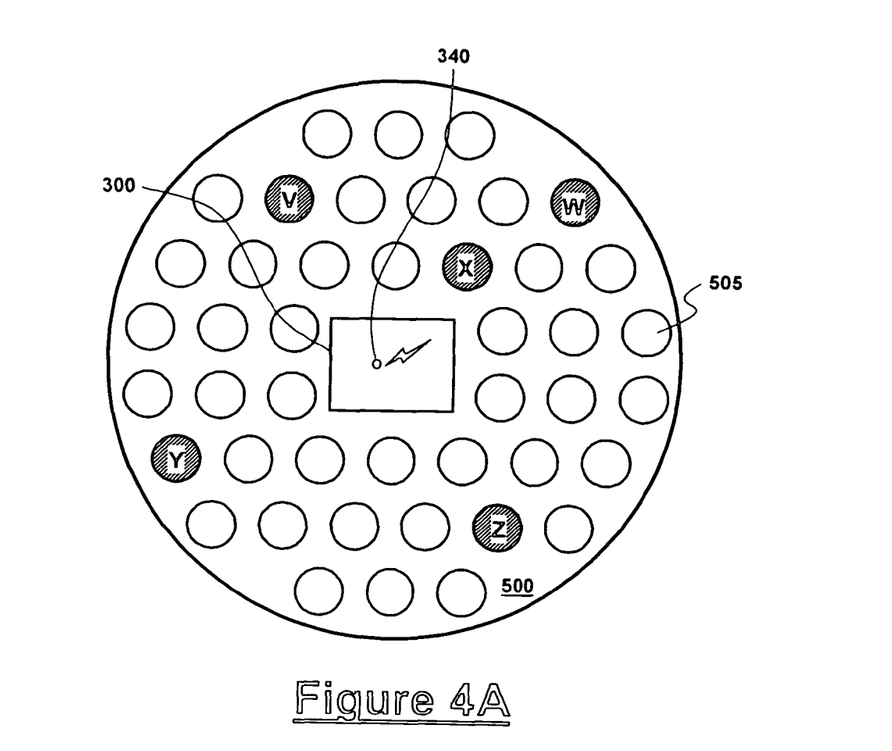
FIGS. 4A & B show a holder/holders with a plurality of samples.
Figure 4B:
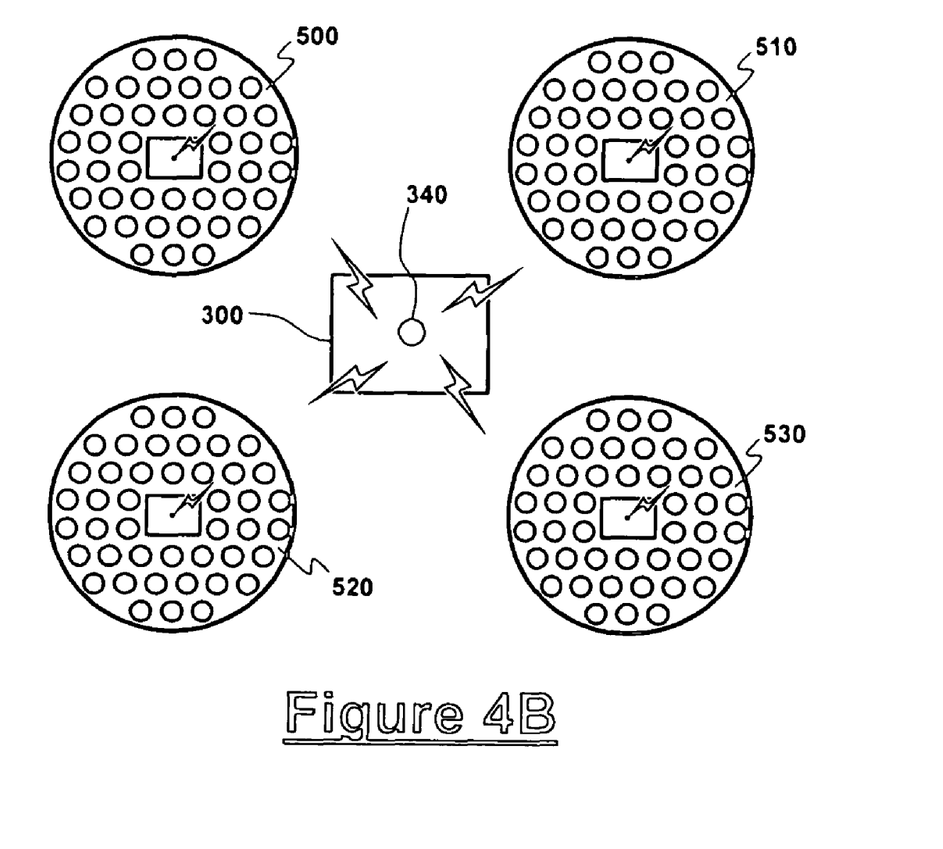

As shown in FIG. 4A, the holder 500 includes a plurality of locations 505 where samples can be disposed in relation to the base station 300. In FIG. 4A only five samples V-Z are placed in the holder. However, the number of samples placed in the holder is limited only by the transmission power and processing capability of the base station 300 and the size of the holder 500. Preferably, the holder 500 is able to control ambient conditions of the samples placed in it. For example, the holder 500 may include one or more of a heater, cooler, pressure chamber, fluid bath, flow cell for passing fluid over selected sensor chips, agitator and so forth. As shown in FIG. 4B, a plurality of holders 500, 510, 520, 530 can be provided for each base station 300, whereby the base station 300 can communicate with each of the sensor chips in each of the samples in each of the holders concurrently. This allows different samples to be measured under different test conditions. This is particularly useful when measuring different redox reactions, which progress at different rates under different measurement conditions. Thus, it is preferable to place samples with sensor chips undergoing redox reactions that take place faster at higher temperatures in heated holders and samples with chips undergoing redox reactions that take place faster at lower temperatures in cooled holders. The different samples may be different samples taken from the same source, for example different parts of one urine sample, or samples from different sources, for example urine samples from different people, or a combination—that is multiple urine samples for each of a number of different people.

Figure 5:
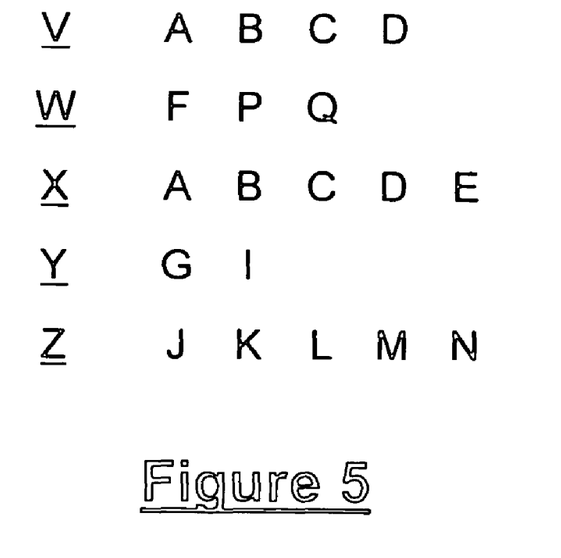
FIG. 5 is a schematic representation of the use of different chips for measuring different properties.

FIG. 5 shows schematically that different chips for measuring different properties are disposed in each of the five samples V-Z shown in FIG. 4A as required. Thus, sample V has chips A-D; sample W has chips F, P and Q; sample X has chips A-E; sample Y has chips G and I; and sample Z has chips J-N. However, the number of sensor chips disposed in a sample is not limited to five. Exemplary properties measured by chips A-E are discussed above. It will be clear to those skilled in the art that chips F-N can be used to measure the presence, absence, and concentration of different target biological molecules. The sensor chips included in each sample are detected in accordance with a recommendation from a physician. For example, it may be intended to determine whether a first subject has or is predisposed to diabetes; whether a second subject providing a sample is HIV positive; whether another subject has diabetes and thyroid problems; whether another subject has malaria; whether another subject is genetically predisposed to cervical and breast cancer and so on.

Figure 6A:
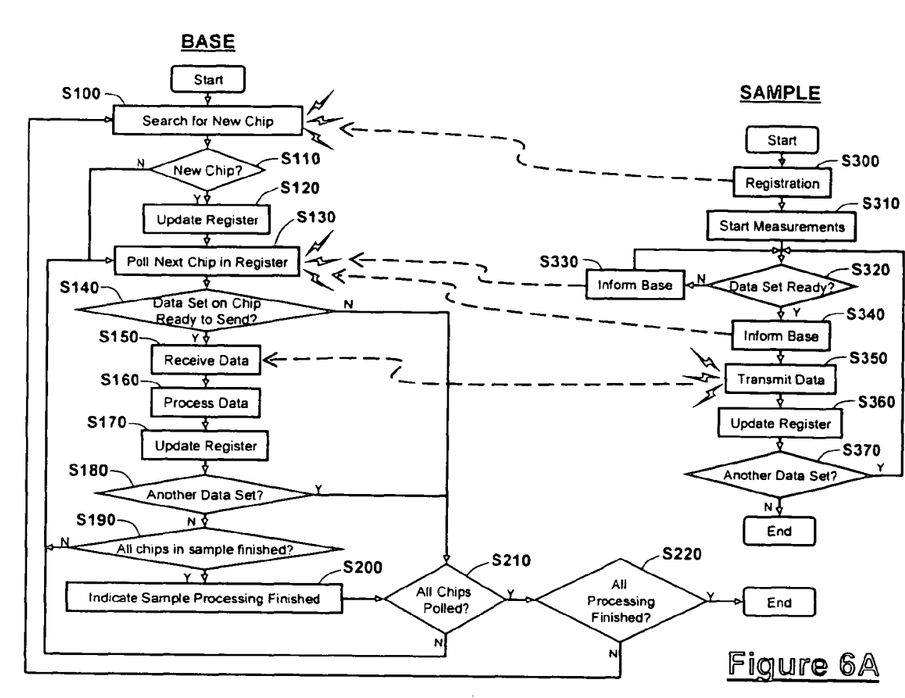
FIG. 6A is a flow chart illustrative of a method according to the present invention.

FIG. 6A is a flow chart illustrative of a method of the present invention. Specifically, FIG. 6 shows the steps followed by both the base station 300 and a sample with a plurality of sensor chips in it to be tested. The base station 300 first searches for previously unrecognised identifiers emitted by RFID devices 120, 210 either on a sensor chip or a sample. When a sample is placed in the holder 500, the RFID circuitry 120 in each sensor chip and in the sample RFID tag 210 extract power from the radio frequency signals emitted by the base station, and the sensor chips and the RFID tag 210 power up. This causes the sensor chips and RFID tags to transmit identification data by radio frequency signals to the base station 300. If it is determined in step S110 that there is new identification data and hence a new sample and new sensor chips, the base station 300 registers the sensor chips and the sample RFID tag 210 in step S120. Preferably, the identification data of the sensor chips includes a portion that is unique to that sensor chip and a portion that indicates the property or properties that that sensor chip is adapted to sense—for example, the particular biological molecule(s) that the sensor chip is adapted to sense. Alternatively, the property or properties that that sensor chip is adapted to sense are stored in the memory 130 of the sensor chip and transmitted to the base station 300. Thus, the register or memory 310 stores each sensor chip ID in association with the property or properties that that sensor chip is adapted to sense. The sample RFID tag has a unique identifier of the sample. If only one sample RFID tag 210 is detected during a step S100 of searching for a new chip, all the sensor chips detected during the same window are associated in the register with that sample. In addition, during or following registration (S300) the new sensor chips are instructed to begin sensing (S310) by the base station 300.

The base station 300 then begins polling the sensor chips that have been registered (S130). In the meantime, each of the sensors on a sensor chip begins measurement and the signals from the sensors are stored in the memory 130 of the sensor chip until the chip is polled. When a chip is polled, the processor 125 in the sensor chip determines whether sufficient data has been stored in the memory 130 since the sensor chip was last polled. If not, the sensor chip informs the base station (S330, S140). The sensor chip then continues to perform a sensing operation (S310) and the base station 300 determines whether all the chips have been polled (S210) and if not polls the next chip (S130). However, if the sensor chip informs the base station that data is ready for transmission (S340), the base station instructs the sensor chip to transmit the sensed data using the RFID electronics (S350). The base station 300 then receives the sensed data from the sensor chip (S150) and stores it in the memory or register 310. The data processing section 320 can then start to process and analyse the data (S160) while the polling sequence continues.

Figure 6B:
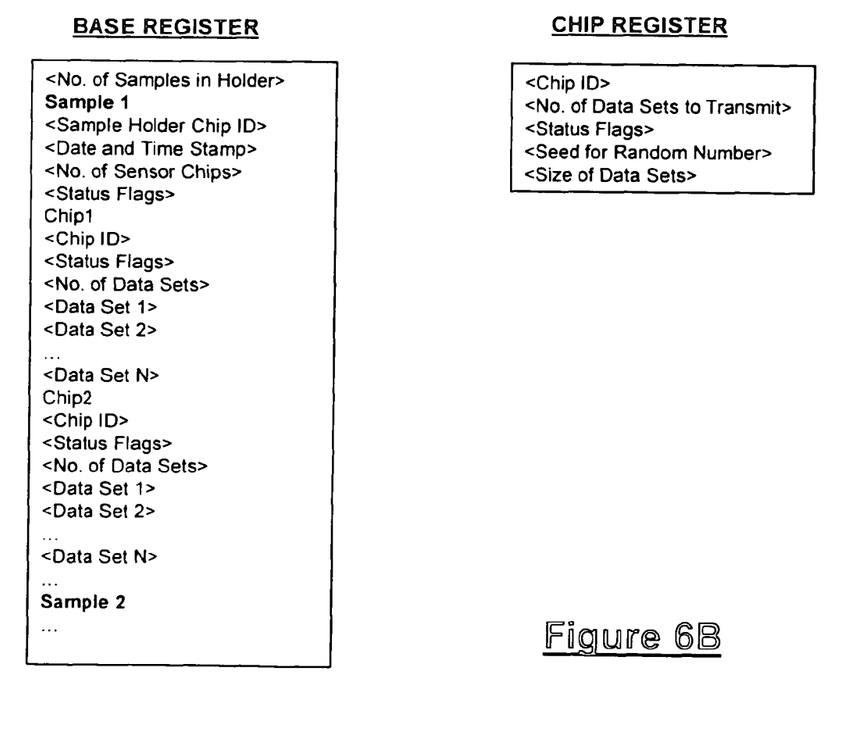
FIG. 6B is a schematic representation of data structures usable in the present invention.

FIG. 6B shows an example of the data structure in the memory or register 310 in the base station 300, and an example of the data structure in the memory 130 of a sensor chip 100.

Either or both the base station and the sensor chip can determine whether the sensor chip has finished performing measurements. For example, the processor 125 of the sensor chip may determine that a redox reaction is complete when the two peaks of the hysteresis loop fall below a predetermined level for a predetermined period. It will then update a flag in the memory 130 and transmit this to the base station 300 the next time it is polled. The base station 300 then updates the register that the sensor chip has finished measurement. Alternatively, the data processing section 320 may determine that measurement is complete, update the register 310 and instruct the sensor chip to switch off.

If the base station establishes in step S170 that measurement for a particular sensor chip is complete and updates the register accordingly in step S180, it then interrogates the register to establish whether measurement has finished for all the sensor chips in a sample (S190) and, if so, indicates this to a user (S200). This may be done, for example, by showing a message on a GUI (such as a computer monitor) or instructing a light on the respective sample RFID tag to illuminate. The user can then remove the sample from the holder 500, thereby freeing up space for the measurement of a further sample. From step S200, or step S170 if it was determined that the sensor chip has not finished measurement, the base station proceeds to step S210, where it is determined whether all the chips have been polled. If not, the base station returns to step S130 and repeats the procedure until all the chips have been polled. Once it is determined that all the chips have been polled, the base station determines whether all processing for all the chips and samples in the holder has finished (S220) and, if so, the process ends. If not, the process returns to the start.

Accordingly, the present invention allows multiple samples to be measured for multiple properties concurrently. Moreover, the samples can be measured under different test conditions to speed up measurement. Once measurement by all chips in a sample has finished, the sample can be removed from the holder and a new sample with different chips can be placed in the holder. At the same time, polling of all the chips in all the samples continues unaffected. Thus, samples can be inserted and removed from the holder without affecting measurement of other samples. Since sensed data from all the sensor chips in a sample is collected and analysed automatically, detection is fast and accurate. Moreover, many different tests can be performed on each sample simultaneously and many different samples can be tested simultaneously. Thus, the present invention allows a very high throughput of samples with increased accuracy.

In a preferred embodiment, selected sensor chips are disposed automatically in a sample and samples are automatically loaded and unloaded from the sensing region—for example, the holder. Thus, the only operation a technician need to perform is to input into the loader or base station controller the identification of the sample and properties being tested for (such as glucose concentration, specified DNA strands, other target biological molecules, pH and so forth). The apparatus of the present invention will then dispose the appropriate sensor chips in the sample, load the sample into the sensing region, collect and analyse sensed data from the sensor chips and provide an indication of the results (for example, negative test result for HIV, positive result for diabetes and so forth). Of course, it is possible to provide considerably more detailed analysis data if desired.

Other advantages of the present invention include that the issues of bulky interconnection between the sensor chips and the data analysis and storage section are removed; that the use of integrated sensing circuits increases the signal-to-noise ratio, allowing smaller sized sensor pads to be used on the sensor chips; multiple chips can be used in a single small-sized sample; different samples can be tested at the same time; the testing of new samples can begin at any time; and the sensor chips can be recycled and reused.

The foregoing description has been given by way of example only and it will be appreciated by a person skilled in the art that modifications can be made without departing from the spirit and scope of the present invention. For example, the term "sample" includes solutions, biological samples such as of urine, blood, serum and so forth, as well as other samples, including solids and gases and combination of them.

In particular, the specific implementation of the sensor chip and base station described above is not limiting. Other forms of wireless communication and identification are also suitable for use in the present invention. In addition, the specific method described above is not to be taken as limiting. In particular, it will be appreciated that several of the steps can be performed in a different order, some steps can be missed out and others steps not herein described can be included.

For example, the sensor chips may transmit to the base station an indication of the frequency or priority they should be given when polling. High priority sensor chips may be polled more frequently than low priority sensor chips. Searching for new chips can also be carried out at the same time as polling.

Various different types of sensor chips may be used and there is no limitation to potentiostat circuit chips. In particular, lab-on-chip type sensor chips fall within the scope of the present invention. Where passive RFID circuitry is provided, the power extraction circuitry will convert the received RF signal to a number of DC levels to power the internal electronics as well as to perform the sensing, for example to monitor a redox bioreaction. However, active RFID circuitry can also be used.

Different embodiments of the holder 500 and the base station are also envisaged. For example, the holder 500 may include means for disposing the sensor chips in flow cells, a centrifuge, pressurising and vacuum means and so forth. The base station 300 may include a computer such as a PC with a monitor and an antenna and transceiver for wireless communication. The samples with sensor chips simply need to be disposed within range of the antenna.

In addition, it is not required to provide the counter electrode 220 from the holder 500 to apply a bias voltage to the sample or solution under test. Rather, each sensor chip may be provided with its own counter electrode for all of the sensors on the chip, or each sensor on the chip may be provided with its own counter electrode.

In the present specification, the terms register, storage means, storage device and memory are interchangeable.

It will be appreciated by those skilled in the art that the method and apparatus of the present invention may incorporate simple error handling coding, such as parity check of the data to reduce bit error during transmission. In addition, receipt of the data may be acknowledged by the base station to the chip to indicate a successful data transfer. Other similar technologies and communications protocols may also be adopted.

What is claimed is:

1. A method of sensing at least one property of each of a plurality of samples, the method comprising:
   disposing at least one sensor chip in each sample, the at least one sensor chip being adapted to sense at least one property of a respective sample and comprising sensing electronics, a wireless communication device and an identifier;
   registering each sensor chip, wherein upon registration, each sensor chip transmits via the wireless communication device of the sensor chip the at least one property that the sensor chip is adapted to sense; and
   receiving sensed data from each registered sensor chip concurrently via the respective wireless communication device; wherein:
   at least one of said sensor chips is a biosensor chip, the biosensor chip being adapted to sense at least one of DNA, RNA, a gene sequence, a peptide and another biological molecule, and
   the biosensor chip includes one or more potentiostat circuits.

2. A method according to claim 1, wherein a counter electrode is provided for each potentiostat circuit in a sample by applying a bias voltage to the sample.

3. A method of sensing at least one property of each of a plurality of samples, the method comprising:
   disposing at least one sensor chip in each sample, the at least one sensor chip being adapted to sense at least one property of a respective sample and comprising sensing electronics, a wireless communication device and an identifier;
   registering each sensor chip, wherein upon registration, each sensor chip transmits via the wireless communication device of the sensor chip the at least one property that the sensor chip is adapted to sense; and
   receiving sensed data from each registered sensor chip concurrently via the respective wireless communication device; wherein:
   the sensor chip is used for sensing one or more properties of a sample using a redox reaction.

4. A method of sensing at least one property of each of a plurality of samples, the method comprising:
   disposing at least one sensor chip in each sample, the at least one sensor chip being adapted to sense at least one property of a respective sample and comprising sensing electronics, a wireless communication device and an identifier;

registering each sensor chip, wherein upon registration, each sensor chip transmits via the wireless communication device of the sensor chip the at least one property that the sensor chip is adapted to sense;

receiving sensed data from each registered sensor chip concurrently via the respective wireless communication device; and disposing a respective sample in a sensing area, the sensing area being adapted to control one or more predetermined conditions of the sample.

5. A method according to claim 4, wherein the sensing area includes at least one of a heater, a cooler, a temperature-controlled fluid bath, an agitator and a means for controlling flow of a fluid to be sampled over the sensor chips.

6. An apparatus for sensing at least one property of each of a plurality of samples concurrently, comprising:
 a sensing area;
 a wireless communication device, the wireless communication device comprising an antenna for wirelessly transmitting signals to and receiving signals from each of a plurality of sensor chips within the sensing area, each sensor chip being disposed in a respective sample, being adapted to sense at least one property of the respective sample and comprising sensing electronics, a sensor chip wireless communication device and an identifier;
 a register for registering the identifier of each sensor chip, wherein upon registration, each sensor chip transmits the at least one property that the sensor chip is adapted to sense to the antenna via the sensor chip wireless communication device for registration; and
 a sensed data processor for receiving and processing sensed data from each of the registered sensor chips concurrently via the sensor chip wireless communication devices; wherein:
 at least one of the plurality of sensor chips is a biosensor chip;
 the sensed data relates to at least one of DNA, RNA, a gene sequence, a peptide and another biological molecule; and
 the biosensor chip includes one or more potentiostat circuits.

7. An apparatus according to claim 6, wherein:
 the apparatus is arranged to apply a bias voltage to a sample in which the biosensor chip is disposed to provide a counter electrode for each potentiostat circuit of the biosensor chip.

8. An apparatus for sensing at least one property of each of a plurality of samples concurrently, comprising:
 a sensing area;
 a wireless communication device, the wireless communication device comprising an antenna for wirelessly transmitting signals to and receiving signals from each of a plurality of sensor chips within the sensing area, each sensor chip being disposed in a respective sample, being adapted to sense at least one property of the respective sample and comprising sensing electronics, a sensor chip wireless communication device and an identifier;
 a register for registering the identifier of each sensor chip, wherein upon registration, each sensor chip transmits the at least one property that the sensor chip is adapted to sense to the antenna via the sensor chip wireless communication device for registration; and
 a sensed data processor for receiving and processing sensed data from each of the registered sensor chips concurrently via the sensor chip wireless communication devices; wherein:
 at least one sensor chip is used for sensing the at least one property of a sample during a redox reaction.

9. An apparatus for sensing at least one property of each of a plurality of samples concurrently, comprising:
 a sensing area;
 a wireless communication device, the wireless communication device comprising an antenna for wirelessly transmitting signals to and receiving signals from each of a plurality of sensor chips within the sensing area, each sensor chip being disposed in a respective sample, being adapted to sense at least one said property of the respective sample and comprising sensing electronics, a sensor chip wireless communication device and an identifier;
 a register for registering the identifier of each sensor chip, wherein upon registration, each sensor chip transmits the at least one property that the sensor chip is adapted to sense to the antenna via the sensor chip wireless communication device for registration; and
 a sensed data processor for receiving and processing sensed data from each of the registered sensor chips concurrently via the sensor chip wireless communication devices; wherein:
 the apparatus is adapted to control at least one condition of samples in the sensing area.

10. An apparatus according to claim 9, wherein the sensing area includes at least one of a heater, a cooler, a temperature-controlled fluid bath, an agitator and a means for controlling flow of a fluid to be sampled over the sensor chips.

* * * * *